United States Patent [19]
Rowland et al.

[11] Patent Number: 5,917,044
[45] Date of Patent: *Jun. 29, 1999

[54] PHENOLIC AMIDES AND THEIR USE AS STABILIZERS

[75] Inventors: Robert G. Rowland, Woodbridge; John R. Baranski, Southington, both of Conn.

[73] Assignee: Uniroyal Chemical Company, Inc., Middlebury, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/839,694

[22] Filed: Apr. 15, 1997

[51] Int. Cl.$^6$ ................................................ C07D 295/00
[52] U.S. Cl. .................... 544/382; 548/568; 544/162; 546/234
[58] Field of Search .................... 548/540, 568; 546/226, 234; 544/391, 176, 162, 382

[56] References Cited

U.S. PATENT DOCUMENTS

| | | | |
|---|---|---|---|
| 3,567,664 | 3/1971 | Haring | 521/117 |
| 3,637,865 | 1/1972 | Haring | 524/258 |
| 3,969,530 | 7/1976 | Mauz et al. | 514/532 |
| 4,066,614 | 1/1978 | Oppelt et al. | 544/391 |
| 4,228,297 | 10/1980 | Haeberli et al. | 546/226 |
| 5,206,414 | 4/1993 | Evans et al. | 546/218 |

OTHER PUBLICATIONS

Minasyan et al; Phenolic acid Derivatives; Arm, Khim, Zh. 39(3), 169–74 1986, (abstract).

*Primary Examiner*—Rachel Gorr
*Attorney, Agent, or Firm*—Raymond D. Thompson; Peter G. Dilworth

[57] ABSTRACT

Phenolic amides, useful as stabilizers for organic materials such as polyols and polyurethanes, possess the general formula

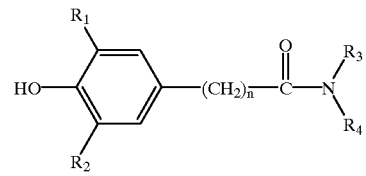

wherein n is 0 to 3, $R_1$, is alkyl of from 1 to about 6 carbon atoms, $R_2$ is hydrogen or alkyl of from 1 to about 6 carbon atoms, $R_3$ is hydrogen or hydrocarbyl of up to about 20 carbon atoms, optionally containing one or more heterocyclic groups, $R_4$ is hydrocarbyl of up to about 20 carbon atoms, optionally containing one or more heterocyclic groups, or $R_3$ and $R_4$ together with the nitrogen atom to which they are bonded are joined together to form a heterocyclic group, optionally containing one or more additional heterocyclic atoms.

2 Claims, No Drawings

PHENOLIC AMIDES AND THEIR USE AS STABILIZERS

BACKGROUND OF THE INVENTION

This invention relates to phenolic amides and the use of the amides as stabilizers for polymers such as polyols and/or polyurethane foams.

The stabilization of polyalkylene polyether polyols and other polymeric materials with antioxidants or other stabilizers and the use of the stabilized polyols in the preparation of polyurethane foams to inhibit scorch are well known to those skilled in the art. Polyether polyols used in the manufacture of slabstock flexible urethane foam are typically stabilized with antioxidant packages consisting of phenolic and amine antioxidants and may also contain the synergist phenothiazine or a phosphate moiety.

Illustrating such stabilization are U.S. Pat. Nos. 3,567,664 and 3,637,865 which disclose polyurethane foams stabilized with a mixture of 2,6-di-tert-butyl-4-methyl phenol [butylated hydroxy toluene (BHT)] and p,p'-dialkyldiphenylamines.

BHT (2,6-di-t-butyl-4-methyl phenol) is the most common and widely used hindered phenolic stabilizer for polyolefins, styrenics, vinyls, and elastomers. However, there are problems associated with the use of BHT such as long term discoloration, high volatility, sublimation, and difficulty of use due to its solid form. Hindered 2,6-di-t-butyl phenolics with various larger aliphatic groups replacing the methyl group in the para-position of the BHT ring have succeeded in reducing volatility, but usually at the expense of a reduction of activity of the antioxidant, as the more substituted compounds contain relatively less of the hindered hydroxy groups which provide the stabilization activity of hindered phenolic stabilizers.

SUMMARY OF THE INVENTION

In accordance with the present invention, phenolic amides are provided which possess the general formula

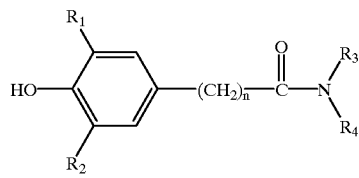

wherein n is 0 to 3, $R_1$, is alkyl of from 1 to about 6 carbon atoms, $R_2$ is hydrogen or alkyl of from 1 to about 6 carbon atoms, $R_3$ is hydrogen or hydrocarbyl of up to about 20 carbon atoms, optionally containing one or more heterocyclic groups, $R_4$ is hydrocarbyl of up to about 20 carbon atoms, optionally containing one or more heterocyclic groups, or $R_3$ and $R_4$ together with the nitrogen atom to which they are bonded are joined together to form a heterocyclic group, optionally containing one or more additional heterocyclic atoms.

The foregoing phenolic amides are useful as stabilizers of organic materials, e.g., polyether polyols to be used in the manufacture of flexible and semiflexible polyurethane foam, which are subject to thermal and oxidative deterioration or degradation caused by heat or light. When added to the polyols and/or directly to the polyurethane foam-forming reaction mixture containing such polyols, the phenolic amide stabilizers inhibit scorch in the polyurethane foam product.

Many of the phenolic amide stabilizers of this invention are less volatile than BHT and as such are less likely to escape into the environment than the latter. Compared to the known esters, the amides of this invention are more resistant to hydrolytic degradation, an advantageous property in those applications where water/moisture may be present. The phenolic amides of this invention possessing one or more amine groups exhibit greater solubility compared with the prior art esters possessing long alkyl chains and are therefore especially advantageous for use in stabilizing polar materials.

DESCRIPTION OF THE PREFERRED EMBODIMENTS

The phenolic amides of this invention are obtained by reacting a phenolic acid or derivative thereof of the general formula

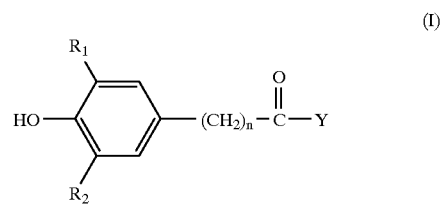

wherein n, $R_1$ and $R_2$ have the aforestated meanings and Y is alkoxy of from 1 to about 20 carbon atoms, hydroxy or halogen, with a primary or secondary alkyl amine of the general formula

wherein $R_3$ and $R_4$ have the aforestated meanings.

Many of the starting phenolic acid compounds and their derivatives are well known. See, e.g., U.S. Pat. Nos. 3,247,240, 3,330,859, 3,364,250, 3,642,868, 3,644,482, 3,801,540, 3,840,585, 4,085,132, 4,228,297, 4,529,809, 4,659,863, 5,089,656, 5,130,465, 5,264,612, and Re. 27,004, the contents of which are incorporated by reference herein. A preferred starting phenolic acid derivative for reaction with a primary or secondary alkyl amine of this invention is methyl 3-(3,5-di-t-butyl-4-hydroxyphenyl) propionate.

Suitable amines for reaction with the foregoing phenolic acids and/or derivatives thereof to provide the phenolic amides of this invention are primary or secondary alkyl amines of aliphatic, cycloaliphatic or aromatic structure optionally containing one or more heteroatoms such as nitrogen, oxygen and/or sulfur. Specific amines include those in which $R_3$ and $R_4$ are independently selected to be methyl, ethyl, propyl, isopropyl, butyl, isobutyl, pentyl, hexyl, cyclohexyl, heptyl, octyl, 2-ethylhexyl, nonyl, decyl, dodecyl, stearyl, oleyl, phenyl, benzyl, and the like, containing e.g., up to about 20 carbon atoms, preferably no more than about 18 carbon atoms and more preferably no more than about 12 carbon atoms. Useful amines in which $R_3$ and $R_4$ together with the nitrogen atom to which they are bonded are joined together to form a heterocyclic compound include cyclic amines such as pyrrolidine, piperidine, piperazine, morpholine, and the like. Also useful are amines in which $R_3$ and/or $R_4$ are alkyl groups substituted with one or more heterocyclic substituents. Examples of such amines are 2-(2-aminoethyl)-1-methylpyrrolidine, 4-(2-aminoethyl)-morpholine, 1-(2-aminoethyl)pyrrolidine, 1-(2-aminoethyl)-piperidine, 1-(2-aminoethyl)piperazine, and the like. Still other useful amines are (aminoalkyl)alkylamines such as N-alkylethylene diamines, N-alkyl-1,3-propane diamines, and the like.

The phenolic amides of this invention are obtained by reacting the phenolic acid or derivative thereof and the primary or secondary alkyl amine in the presence of a suitable catalyst, e.g., p-toluene sulfonic acid. The reaction is advantageously conducted in a subsurface gas purge such as nitrogen. A preferred temperature for this reaction is from about 110° C. to about 250° C. and more preferably from about 130° C. to about 180° C.

The phenolic amides of this invention are useful as stabilizers for organic materials that are susceptible to degradation, e.g., deterioration due to oxidation, elevated temperature and/or exposure to light or other actinic radiation. Examples of such organic materials are synthetic organic polymers such as vinyl resins formed from the polymerization of vinyl halides or from the copolymerization of vinyl halides with unsaturated polymerizable compounds. Examples of these unsaturated polymerizable compounds include vinyl esters, alpha, beta-unsaturated acids, esters, aldehydes, or ketones, and unsaturated hydrocarbons such as butadiene or styrene.

Additional materials stabilized by the phenolic amide stabilizers of this invention are poly-alpha-olefins such as polyethylene, polypropylene, polybutylene, and polyisoprene, copolymers of poly-alpha-olefins, polyamides, polyesters, polycarbonates, polyacetals, polystyrene, and polyethylenoxide. Also included are copolymers such as high-impact polystyrene containing copolymers of butadiene and styrene and those formed by the copolymerization of acrylonitrile, butadiene, and styrene.

Other materials also stabilized include aliphatic ester lubricating oils, animal and vegetable-derived oils, hydrocarbon materials such as gasoline, diesel oil, mineral oil, fuel oil, drying oil, cutting fluids, waxes, resins, and fatty acids such as soaps.

The phenolic amides of this invention are particularly useful for the stabilization of polyether polyols and polyurethane foams derived therefrom. Stabilization is required to protect these materials from oxidative degradation, particularly at the high temperature encountered during the reaction to make polyurethane foam. Polyether polyols are well known in the art and are obtained by reacting polyhydric alcohols, e.g., those containing from 2–8 hydroxyl groups such as ethylene glycol, propylene glycol, diethylene glycol, 2,3-butylene glycol, 1,3-butylene glycol, 1,5-pentane diol, glycerol, trimethylolpropane, triethylolpropane, sorbitol, pentaerythritol, and mixtures thereof, with a 1,2-epoxide, e.g., ethylene oxide, propylene oxide, butylene oxide, cyclohexane oxide, glycidol and mixtures thereof. The preferred polyether polyols contain from 2–4 hydroxyl groups and are obtained by reacting one or more polyhydric alcohols having a like number of hydroxyl groups with ethylene oxide, propylene oxide, butylene oxide, and mixtures thereof.

The phenolic amide stabilizer is added to the polyether polyol in an amount sufficient to impart an appreciable stabilizing effect. In general, this amount may vary from about 0.1 to about 2 weight percent, preferably from about 0.2 to about 1 weight percent and more preferably from about 0.4 to about 0.6 weight percent by total weight of polyether polyol.

Where the polyether polyol is to be employed in the manufacture of a polyurethane foam, and stabilization of the polyol is not in issue, the stabilizer composition can be added to some other component of the polyurethane-forming reaction mixture, e.g., to the polyisocyanate, the prepolymer, the foaming agent, etc., or to the reaction mixture once formed, rather than to the polyol. In this case, the foregoing amounts of phenolic amide stabilizer calculated on the basis of the total polyether polyol component can be utilized.

Any suitable organic isocyanate which is capable of reacting with a polyol to form a polyurethane can be employed in preparing the foam. This includes diisocyanates and polyisocyanates, e.g., triisocyanates and polymeric isocyanates. Due to their commercial availability, the polymeric isocyanates and toluene diisocyanates are preferred. The latter, the use of which is more preferred, can be supplied in the form of an isomeric mixture of about 80 weight percent of the 2,4-isomer and about 20 weight percent of the 2,6-isomer. Other typical isocyanates include 4,4'-methylene-bis(phenylisocyanate), 3,3'-bitolylene-4,4'-diisocyanate, 3,3'-dimethoxy-biphenylene-4,4'-diisocyanate, naphthalene-1,5-diisocyanate, hexamethylene diisocyanate, 1,4-phenylene diisocyanate, polyphenylene polymethylene isocyanate, etc. The amount of isocyanate employed in the preparation of the polyurethane foams should be sufficient to provide at least about 0.7 NCO groups per hydroxyl group present in the reaction system. An excess of isocyanate compound can be conveniently employed, however, the use of a large excess is generally undesirable due to the high cost of the isocyanate compounds. It is preferable, therefore, to employ no greater than about 1.5 NCO groups per hydroxyl group, and still more preferably from about 0.9 to about 1.3 NCO groups per hydroxyl group.

In preparing the polyurethane foams, the polyol containing the phenolic amide stabilizer of this invention is reacted with the organic isocyanate in the presence of a foaming agent and a reaction catalyst. The foaming agent can be any of those known to be useful for this purpose, e.g., water. The amount of foaming agent employed can be varied within a wide range. Generally, water is employed in an amount of from about 0.1 to about 10 parts by weight of the polyol.

The catalyst used in preparing the polyurethane foams can be any of those known to be useful for this purpose or mixtures thereof, including tertiary amines and metallic salts. Typical tertiary amines include N-methyl morpholine, N-hydroxyethyl morpholine, triethylene diamine, dimethyl ethanolamine, tetramethylbutane diamine, trimethylamine, triethylamine, etc. Typical metallic salts include the salts of antimony, tin, and iron, e.g., dibutyltin dilaurate, stannous octanoate, etc. Generally speaking, the catalyst is employed in an amount ranging from about 0.1 to about 2.0 weight percent based on the weight of the polyol.

It is preferred in the preparation of the polyurethane foams of the present invention to employ minor amounts of a surfactant in order to improve the cell structure of the polyurethane foams. Typical of such surfactants are the silicon-based surfactants as disclosed, e.g., in U.S. Pat. No. 2,834,748 and in the book "Rigid Plastic Foams" by T. H. Ferrigno (1963), Reinhold Publishing Company. Other suitable compounds useful as surfactants include synthetic detergents such as oxyethylated nonyl phenol and other ethylene oxide and glycidol-based surfactants. Generally up to about 2 parts by weight of the surfactant is employed per 100 parts by weight of polyol.

Various additives can also be employed in preparing the foam which serve to provide different properties. Fillers, e.g., clay, calcium sulfate, barium sulfate, ammonium phosphate, etc., can be added to lower cost and improve physical properties. Dyes can be added for color and fibrous glass or synthetic fibers can be added for strength. In addition, plasticizer, deodorants and flame retardants can be added.

The following examples are illustrative of the invention.

Microwave Oven Scorch Test

The Microwave Oven Scorch Induction Test (MOSIT) is a rapid, reproducible bench scale test for the effectiveness of antioxidant packages which correlates well with observed results from large scale industrial foams. This procedure utilizes small hand-mixed foam buns to evaluate the effectiveness of antioxidant packages. Because small buns will dissipate the internal heat more rapidly than foam buns produced on an industrial scale, a microwave oven is used to uniformly heat the foam bun by radiant energy, rather than conducting heat through it by the use of a convection oven. The microwave oven promotes heating of the small foam bun under conditions which have the ability to create reproducible scorch within the foam bun. Because humidity and temperature in the laboratory can affect results, it is advisable for antioxidant package comparisons to be run concurrently.

The formulation used to prepare foam bun samples is listed in Table I and is typical of what is currently used by many major U.S. polyol manufacturers in similar type testing.

TABLE 1

Flexible slabstock foam formulation.

| | |
|---|---:|
| Stabilized polyether polyol* | 200.0 grams |
| Water (de-ionized) | 10.0 grams |
| Amine catalyst (Dabco 33-LV, Air Products) | 0.5 grams |
| Surfactant (Niax L-620, Air Products) | 2.0 grams |
| Flame retardant (Fyrol FR-2, AKZO) | 12.0 grams |
| Tin catalyst (Dabco T- 1 0, Air Products) | 0.4 grams |
| Toluene Diisocyanate (TDI-80/20, Olin) | 124.5 grams |
| TDI index | 109 |

*Polyether polyol - A 3,000 average molecular weight polyol, when received contains a minimum stabilization of approximately 100 ppm butylated hydroxytoluene (BHT). This polyol is then further stabilized with AO package to be evaluated.

The microwave oven employed in this testing was a 700 watt Whirlpool TimeMaster. Prior to testing the first foam bun, the microwave oven is pre-conditioned by placing a 1000 mL beaker containing 600 mL of water in the microwave oven for 30 minutes at a power setting of 60%. A fresh beaker is returned to the microwave oven for 15 minutes at a power setting of 60% prior to each additional foam bun tested. This procedure is carried out in order to maintain a constant temperature and humidity within the microwave oven during testing.

The prepared foam formulation is poured into a 10"×10"× 5" cardboard box and allowed to rise. Five minutes after the appearance of health bubbles across the surface of the foam bun, the sides of the cardboard box are removed. The foam bun is immediately placed into the preconditioned microwave oven. The foam is irradiated for a specified time (usually about 15 minutes) at a power setting of 30%. The foam bun is removed from the microwave oven, and immediately placed into an air circulating oven for 3 minutes at 125° C., to cure the hide of the foam. Upon removal from the air circulating oven, the foam bun is immediately cut in half, perpendicular to the rise of the foam, and inspected for degree of scorch. A rating of "0" indicates no scorch while a rating of "10" indicates very severe scorch. Two foams of each formulation were prepared. The scorch ratings of each formulation were averaged to give the results disclosed below.

EXAMPLE 1

This example illustrates the preparation and testing of the compound

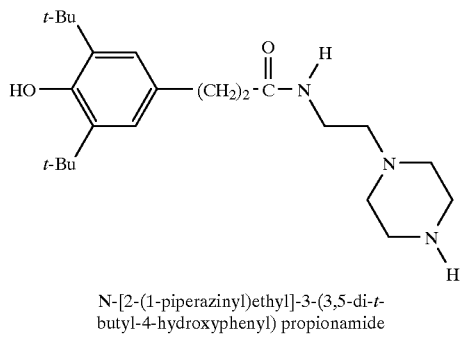

N-[2-(1-piperazinyl)ethyl]-3-(3,5-di-*t*-butyl-4-hydroxyphenyl) propionamide

Preparation

To a 250 mL 3-neck round-bottom flask equipped with an overhead stirrer, a sub-surface nitrogen purge and a condenser, a mixture of 53.46 g (0.183 mol) of methyl 3-(3,5-di-t-butyl-4-hydroxyphenyl) propionate with 48.0 mL (0.366 mol) of 1-(2-aminoethyl)-piperazine and 0.94 g (0.0049 mol) p-toluene sulfonic acid monohydrate was added. The reaction mixture was then stirred at 140° C. for 15 hours with a moderate nitrogen purge to produce a thick orange-yellow final product.

To the thick orange-yellow final product, 100 mL portion of reagent xylenes was added. The product was washed two times with 100 mL of hot (90° C.) 0.1M sodium bicarbonate solution and then washed twice with 100 mL hot (90° C.) de-ionized water. The solvent was removed using a rotary evaporator. The final crude product was a light orange-yellow glassy solid at 25° C.

A 24 g portion of the final product was vacuum distilled. The distillate was a light yellow, glassy solid at 25° C. with a melting point of 50 to 55° C. A 5 g sample of the distillate was recrystallized from xylenes having a melting point of 109 to 111° C.

Testing a) The following polyether polyol samples were prepared:
1. Standard containing 2500 ppm BHT and 2000 ppm Naugard-445.
2. Experimental sample containing 2500 ppm of Example 1.

| Results: | | |
|---|---:|---:|
| Polyol Sample | 1 | 2 |
| Naugard-BHT ppm | 2500 | 0 |
| Naugard-445 ppm | 2000 | 2000 |
| Example 1 | 0 | 2500 |
| Scorch Number* | 2.0 | 2.0 |

*Scorch Number = 0–10, where 0 = no scorch and 10 = very severe scorch.

b) A repeat of Test (a) was conducted. The following polyether polyol samples were prepared:
1. Standard containing 2500 ppm BHT and 2000 ppm Naugard-445.
2. Experimental sample containing 2500 ppm of Example 1.

| Results: | | |
|---|---|---|
| Polyol Sample | 1 | 2 |
| Naugard-BHT ppm | 2500 | 0 |
| Naugard-445 ppm | 2000 | 2000 |
| Example 1 | 0 | 2500 |
| Scorch Number* | 1.0 | 1.0 |

*Scorch Number = 0–10, where 0 = no scorch and 10 = very severe scorch.

The result of this test was that equivalent performance was repeated.

c) Thermogravimetric Analysis of Example 1 versus BHT

This experiment was conducted to determine the volatility of the phenolic amide stabilizer versus BHT.

Thermogravimetric Analysis (TGA) of neat antioxidants was a technique used to measure volatility. Approximately 10 mg of sample is weighed into an aluminum sample cup and then placed inside the chamber of a Perkin-Elmer TGS-2 Thermogravimetric Analyzer. The chamber was equilibrated to 160° C. under a nitrogen flow of 50 mL per minute, and run isothermally for 250 minutes or until 100% weight loss of the sample is experienced. A temperature of 160° C. was used since it approximates temperatures reached during production of large scale industrial foams.

Results

After 10 minutes at 160° C. with a nitrogen flow of 50 mL/minute, 72% of the BHT had volatilized. After 250 minutes, only 1.6 percent of Example 1 had volatilized.

EXAMPLE 2

This example illustrates the preparation and testing of the compound

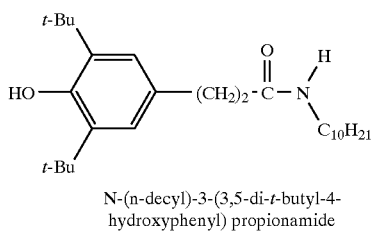

N-(n-decyl)-3-(3,5-di-t-butyl-4-hydroxyphenyl) propionamide

Preparation

To a 100 mL 3-neck, round-bottom flask equipped with an overhead stirrer, a subsurface nitrogen purge and a condenser, 21.7 g (0.074 mol) of methyl 3-(3,5-di-t-butyl-4-hydroxyphenyl) propionate with 21.5 g (0.137 mol) of decyl amine and 0.47 g (0.0025 mol) p-toluene sulfonic acid monohydrate was added. The mixture was stirred at 170° C. for 15 hours with a moderate nitrogen purge.

15 mL reagent xylenes was then added to dissolve the final product. The product was washed two times with a 50 mL portion of hot (90° C.) 0.1M sodium bicarbonate solution and then washed three times with 50 mL portions of hot (90° C.) de-ionized water. The solvent was removed using a rotary evaporator and 27.7 g of a viscous yellow liquid was recovered. The liquid was crystallized over a two week period with the crystallized product having a melting point of 52 to 56° C.

Testing

The following polyether polyol samples were prepared:

1. Standard containing 2500 ppm BHT and 2000 ppm Naugard-445.
2. Experimental sample containing 2500 ppm Example 2 and 2000 ppm Naugard-445.

| Results: | | |
|---|---|---|
| Polyol Sample | 1 | 2 |
| Naugard-BHT ppm | 2500 | 0 |
| Naugard-445 ppm | 2000 | 2000 |
| Example 2 | 0 | 2500 |
| Scorch Number | 3.0 | 3.0 |

*Scorch Number = 0–10, where 0 = no scorch and 10 = very severe scorch.

These results indicate equivalent performance of the experimental and the standard containing BHT.

EXAMPLE 3

This example illustrates the preparation and testing of the compound

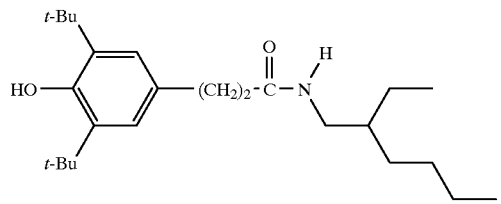

N-(2-ethylhexyl)-3-(3,5-di-t-butyl-4-hydroxyphenyl) propionamide

Preparation

To a 100 mL 3-neck round-bottom flask equipped with an overhead stirrer, a subsurface nitrogen purge and a 70° C. knock-back condenser, a mixture of 35.0 g (0.120 mol) of methyl 3-(3,5-di-t-butyl-4-hydroxyphenyl) propionate with 23.2 g (0.180 mol) of 2-ethylhexyl amine and 0.16 g lithium amide was added. The reaction mixture was stirred at 160° C. for 15 hours with a moderate nitrogen purge.

The viscous light-yellow product was dissolved in 50 mL reagent xylenes and washed with 200 mL 0.3M HCl. The product was then washed five times with 200 mL portions of de-ionized water. A rotary evaporator was used to remove the solvent and 42.1 g of a light yellow viscous liquid was recovered. The product was crystallized over a four week period with the crystallized product having a melting point of 62 to 64° C.

Testing a) The following polyether polyol samples were prepared:

1. Standard containing 2500 ppm BHT and 2000 ppm Naugard-445.
2. Experimental sample containing 2500 ppm Example 3 and 2000 ppm Naugard-445.

| Results: | | |
|---|---|---|
| Polyol Sample | 1 | 2 |
| Naugard-BHT ppm | 2500 | 0 |
| Naugard-445 ppm | 2000 | 2000 |
| Example 3 | 0 | 2500 |
| Scorch Number* | 2.0 | 1.5 |

*Scorch Number = 0–10, where 0 = no scorch and 10 = very severe scorch.

b) A repeat of Test (a) using PS-30 (a liquid amine commercially available from Uniroyal Chemical Co.) as the amine stabilizer.

The following polyether polyol samples were prepared:

1. Standard containing 2500 ppm BHT and 2000 ppm Naugard-445.

2. Experimental containing 2500 ppm Example 3 and 2000 ppm Naugard PS-30.

| Results: | | |
|---|---|---|
| Polyol Sample | 1 | 2 |
| Naugard-BHT ppm | 2500 | 0 |
| Naugard-445 ppm | 2000 | 0 |
| Naugard PS-30 | 0 | 2000 |
| Example 3 | 0 | 2500 |
| Scorch Number* | 3.00 | 2.75 |

*Scorch Number = 0–10, where 0 = no scorch and 10 = very severe scorch.

There was a noticeable improvement in scorch protection using the experimental stabilizer package versus the standard.

What is claimed is:

1. A phenolic amide compound of the general formula

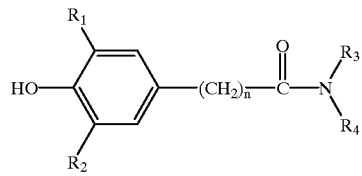

wherein n is 0 to 3, $R_1$ alkyl of from 1 to about 6 carbon atoms. $R_2$ is hydrogen or alkyl of from 1 to about 6 carbon atoms it being provided that at least one of $R_1$ and $R_2$ is t-butyl, $R_3$ is hydrogen and $R_4$ is alkyl of up to about 20 carbon atoms containing a heterocyclic group.

2. A phenolic amide compound which is N-[2-(1-piperazinyl)ethyl]-3-(3,5-di-t-butyl-4-hydroxyphenyl)propionamide.

* * * * *